United States Patent
Burns et al.

(10) Patent No.: US 7,650,028 B1
(45) Date of Patent: Jan. 19, 2010

(54) VICINAL LIGHT INSPECTION OF TRANSLUCENT MATERIALS

(75) Inventors: Geroge R. Burns, Albuquerque, NM (US); Pin Yang, Albuquerque, NM (US)

(73) Assignee: Sandia Corporation, Alburquerque, NM (US)

( * ) Notice: Subject to any disclaimer, the term of this patent is extended or adjusted under 35 U.S.C. 154(b) by 0 days.

(21) Appl. No.: 12/328,472

(22) Filed: Dec. 4, 2008

Related U.S. Application Data

(63) Continuation-in-part of application No. 11/060,130, filed on Feb. 17, 2005, now abandoned.

(60) Provisional application No. 60/622,175, filed on Oct. 26, 2004.

(51) Int. Cl.
G06K 9/00 (2006.01)
G06K 9/66 (2006.01)
G01N 21/85 (2006.01)
G01N 21/00 (2006.01)

(52) U.S. Cl. ............... 382/141; 382/149; 382/190; 356/237.1; 356/239.1; 250/574

(58) Field of Classification Search ............... 382/145, 382/154, 151, 141, 149; 250/306, 307, 310; 356/237.01, 237.5, 239.1, 237.1
See application file for complete search history.

(56) References Cited

U.S. PATENT DOCUMENTS

| | | | | |
|---|---|---|---|---|
| 5,699,153 A * | 12/1997 | Takamoto et al. | ........ | 356/237.1 |
| 5,894,345 A * | 4/1999 | Takamoto et al. | ........ | 356/237.1 |
| 5,943,437 A * | 8/1999 | Sumie et al. | ........ | 382/149 |
| 6,124,926 A | 9/2000 | Ogawa et al. | | |
| 6,498,867 B1 * | 12/2002 | Potucek et al. | ........ | 382/274 |
| 6,525,810 B1 * | 2/2003 | Kipman | ........ | 356/237.1 |
| 6,556,291 B2 * | 4/2003 | Yonezawa | ........ | 356/237.2 |
| 6,556,293 B2 | 4/2003 | Savareigo | | |
| 6,621,572 B2 | 9/2003 | Savareigo | | |
| 6,937,754 B1 * | 8/2005 | Eguchi | ........ | 382/145 |
| 6,965,429 B2 * | 11/2005 | Honda et al. | ........ | 356/237.1 |
| 2003/0025907 A1 | 2/2003 | Savareigo | | |
| 2003/0043369 A1 | 3/2003 | Smith | | |
| 2003/0210391 A1 * | 11/2003 | Uto et al. | ........ | 356/237.1 |
| 2003/0227617 A1 * | 12/2003 | Yoshida et al. | ........ | 356/237.1 |
| 2004/0066962 A1 * | 4/2004 | Sasa et al. | ........ | 382/141 |

OTHER PUBLICATIONS

Burns, G.R., et al., "Study of Methods for Automated Crack Inspection of Electrically Poled Piezoelectric Ceramics", SAND2004-1934, Printed Jun. 2004.

(Continued)

*Primary Examiner*—Wesley Tucker
*Assistant Examiner*—Andrae S Allison
(74) *Attorney, Agent, or Firm*—William R. Conley

(57) ABSTRACT

The present invention includes methods and apparatus for inspecting vicinally illuminated non-patterned areas of translucent materials. An initial image of the material is received. A second image is received following a relative translation between the material being inspected and a device generating the images. Each vicinally illuminated image includes a portion having optimal illumination, that can be extracted and stored in a composite image of the non-patterned area. The composite image includes aligned portions of the extracted image portions, and provides a composite having optimal illumination over a non-patterned area of the material to be inspected. The composite image can be processed by enhancement and object detection algorithms, to determine the presence of, and characterize any inhomogeneities present in the material.

15 Claims, 13 Drawing Sheets

OTHER PUBLICATIONS

Burns, G.R., et al., "Automatic Crack Inspection of PSZT Bars", a posteer presented at: Rio Grande Regional Symposium and Advanced Materials Conference, Albuquerque, NM Oct. 27, 2003.

Hull, "Nondestructive Detection of Cracks in Ceramics Using Vicinal Illumination", EEE links, vol. 6, No. 1, Mar. 2000, pp. 13-20.

* cited by examiner

VICINAL LIGHT INSPECTION OF TRANSLUCENT MATERIALS

CROSS-REFERENCE TO RELATED APPLICATIONS

This application is a continuation-in-part of U.S. patent application Ser. No. 11/060,130 filed on Feb. 17, 2005 now abandoned. This application claims the benefit of U.S. Provisional Application No. 60/622,175 filed on Oct. 26, 2004. The entirety of the disclosures of each of which is herein incorporated by reference.

STATEMENT REGARDING FEDERALLY SPONSORED RESEARCH OR DEVELOPMENT

The United States Government has certain rights in this invention pursuant to Department of Energy Contract No. DE-AC04-94AL85000 with Sandia Corporation.

FIELD OF THE INVENTION

The present invention relates to methods and apparatus for the visual inspection of non-patterned translucent materials. The present invention further relates to the inspection of non-patterned portions of translucent substrates to allow detection of cracks, chips, voids and similar defects in an otherwise homogeneous surface.

BACKGROUND OF THE INVENTION

Translucent materials such as ceramics and glasses, are prone to cracking from a variety of stress sources throughout their manufacturing cycle. Detecting cracks, voids and other inhomogeneities in or on a homogenous surface early in the production process, for example of electrical and/or optical components, beneficially avoids detecting a defect later in the production process and losses from the accumulated costs associated with processing an initially defective substrate. Later in the production cycle, pattern recognition methods as known in the art may be applied to a substrate having been processed to have a pattern on or in the surface of the substrate, which are in contrast to the present inventive methods that do not involve pattern recognition techniques and are applicable to otherwise homogenous (i.e. non-patterned) substrates or portions of a substrate's surface not comprising a pattern. It is well known that the application of pattern recognition inspection methods to a non-patterned substrate or non-patterned area of a substrate are fundamentally destined to fail, as there is no pattern to compare to a known-good or expected pattern. Furthermore, the present inventive methods are not applicable to patterned areas of a substrate as the pattern itself would be identified as an inhomogeneity in the surface of the substrate and perhaps falsely indicate a defect, or as well the pattern itself could mask or cover-up a defect in the underlying substrate, which is an object of the present invention to detect.

As defined herein, translucent materials are materials wherein at least a portion of light from an illumination source penetrates the surface of the material. By this definition, translucent materials include transparent and semi-transparent materials, such as glasses, ceramics and combinations thereof. Stresses in these materials can arise from; an inhomogeneous density distribution in the green body during ceramic forming and sintering, component machining and handling, and thermal stresses developed during sudden temperature changes, all of which can result in crack initiation in the material. For piezoelectric ceramic components, electromechanical stresses can also be created during a hot poling process, which can lead to crack formation. Unlike cracks created by forming operations and thermal-shock, cracks generated during machining, handling and hot poling are small and difficult to detect. These cracks can have a crack opening width of less than 1 μm, are typically found near the edges of a component, and can be of concern when their length exceeds about 25 μm. The presence of cracks, defects and other inhomogeneities in glass, ceramic and glass-ceramic substrates, is a potential source of unreliable functionality. Thus routine yet robust inspection methods are needed for crack detection and characterization of non-patterned (i.e. unpatterned) substrates (i.e. or non-patterned portion thereof).

The present invention provides methods and apparatus for inspecting, detecting and characterizing cracks, defects and other inhomogeneities as may be found in the otherwise homogeneous surface (i.e. non-patterned) of glass, ceramic and glass-ceramic materials, that are translucent to an illumination source.

BRIEF DESCRIPTION OF THE DRAWINGS

The accompanying drawings, which are incorporated in and form part of the specification, illustrate several embodiments of the present invention and, together with the description, serve to explain the principles of the invention. The drawings provided herein are not drawn to scale.

DETAILED DESCRIPTION OF THE INVENTION

Figure 1:
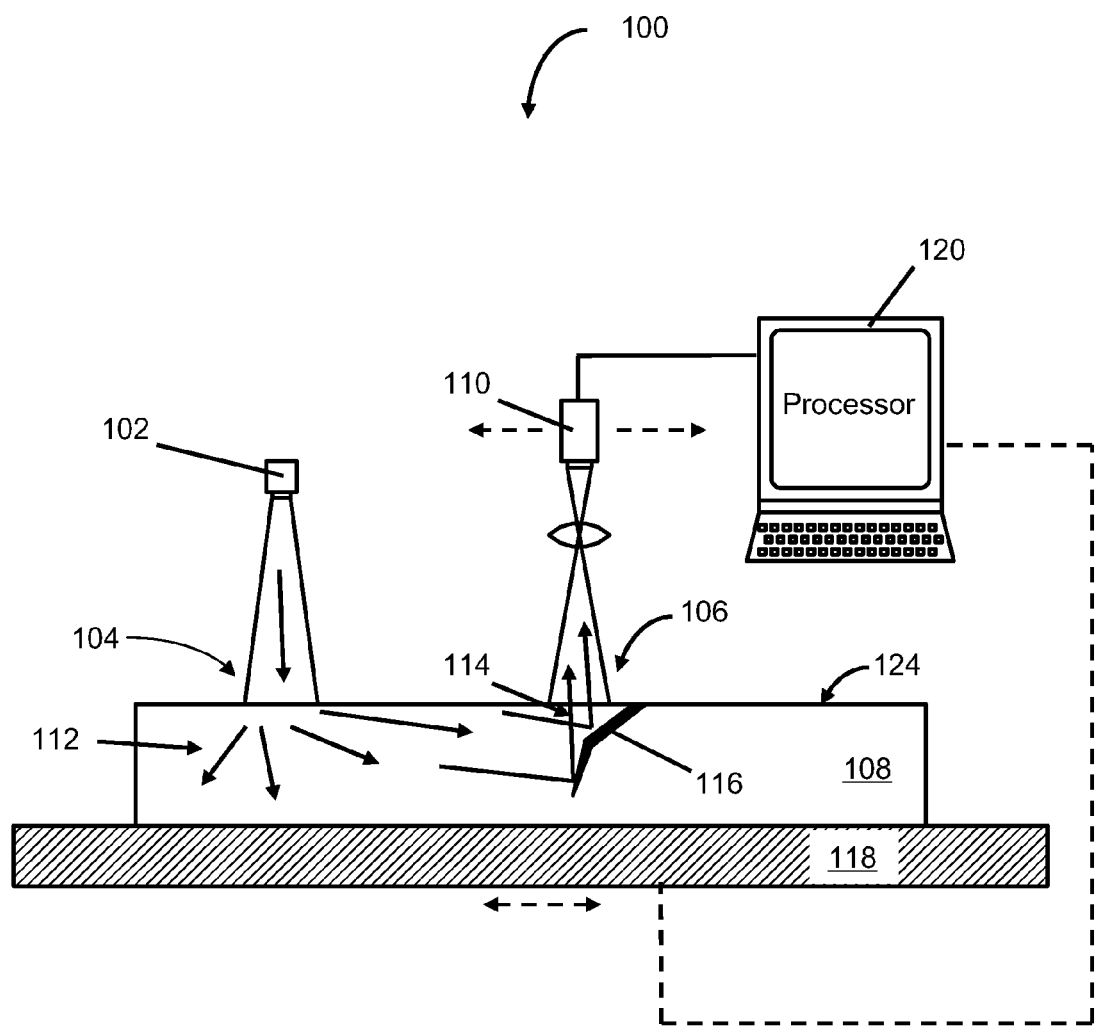
FIG. 1 is a schematic illustration of a vicinally illuminated inspection system.

FIG. 1 is a schematic illustration of a vicinally illuminated inspection system 100. Light from an illumination source 102 illuminates an area 104 on a surface 124 of an otherwise homogenous translucent material 108 that can be in the form of a substrate. A camera 110 (i.e. an imaging device) observes an area 106 not comprising a pattern, displaced from the illuminated area 104 (i.e. vicinal illumination). Light from the illumination source 102 penetrates the surface 124, and diffuses 112 through the interior of the substrate 108. The diffused light 112 traverses through the substrate whereupon it may encounter an inhomogeneity 116 (e.g. a crack, a void, an inclusion etc.). The diffused light 112 is reflected off the inhomogeneity 116 and exits the surface 124 as diffused reflected light 114. The diffused reflected light 114 is imaged by the camera 110. Image data from an imaging device is received by a processor 120. Note that in the inspection of the surface 124 the area being inspected 106 is presumed to be homogeneous (e.g. as in a non-patterned area) and an object of the present invention is to detect inhomogeneities (e.g. 116) in the surface as potential defects in the material 108. The present invention is not applicable to the inspection of patterned areas of a material 108 nor do pattern recognition methods obviate the present invention.

The substrate 108 is translatable relative to the illumination source 102 and the camera 110. A method for accomplishing the relative translation is to support the substrate 108 on a translatable stage 118. The displacement of the stage 118 can be controlled by the processor 120 (as illustrated by the dotted interconnection). An alternative method for accomplishing a relative translation between the substrate 108 and an imaging device 110, is to fix the position of the substrate 108 and translate the camera 110. Images are sequentially generated as a relative translation occurs between the substrate 108, and the imaging device 110. Each image in the sequence comprises an area of the substrate that is adjacent to (or overlapping), and aligned with, the area of the substrate captured in preceding and subsequent images. Imaging device 110 can comprise a camera or any one of a variety of digital imaging devices including CMOS and CCD technologies. Alternatively, photographic (i.e. print) images of the substrate 108 can be translated into a data format by means of scanner (not shown), the data generated by the scanner then being received by the processor 120. The processor 120 can comprise a computer, a PC (personal computer), a laptop PC, an ASIC (application specific integrated circuit), a PLC (programmable logic controller), a microprocessor, or other suitable processing device.

Figure 2:
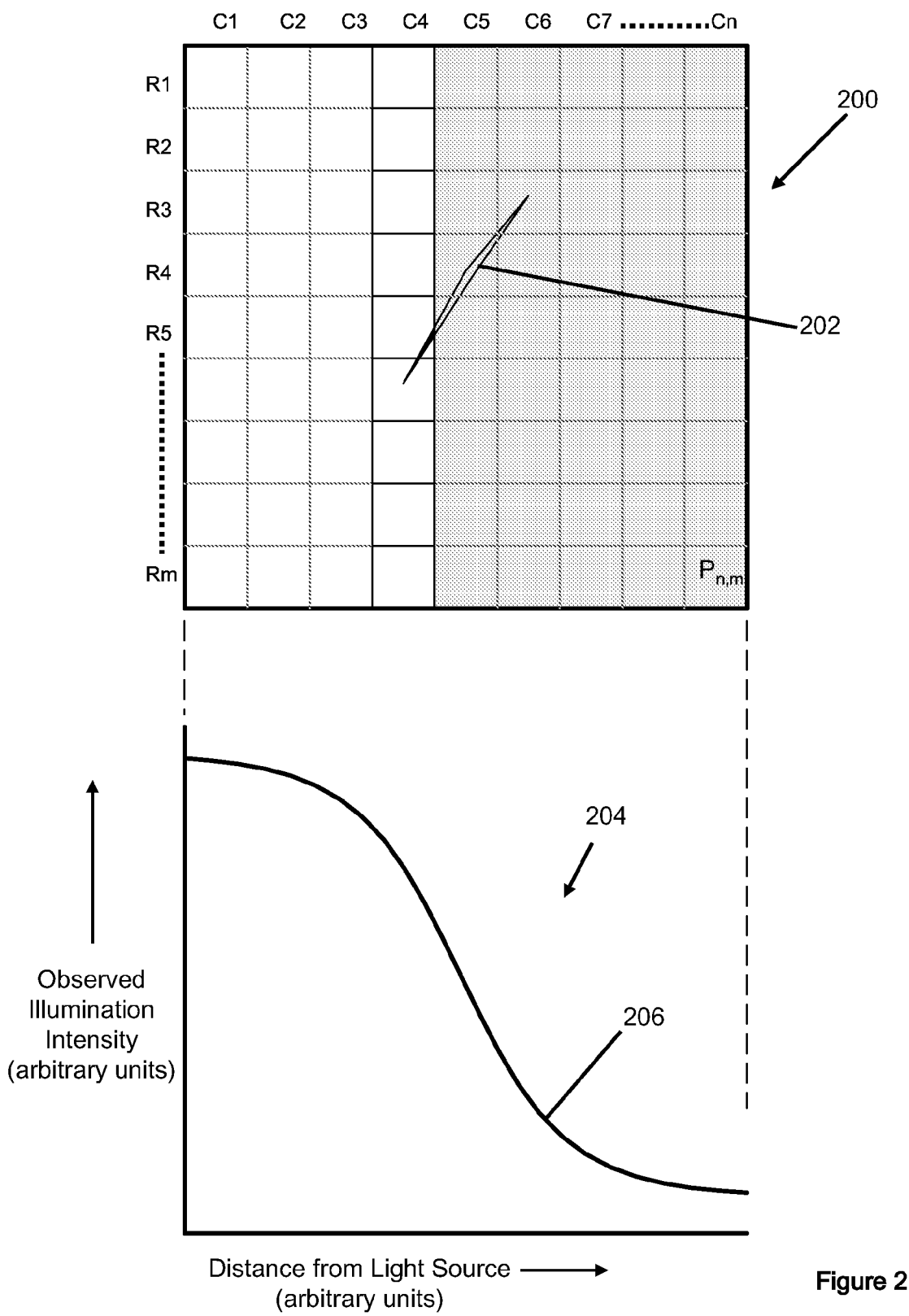
FIG. 2 is a schematic illustration of an image produced by vicinal illumination, and illustrates a variation of illumination intensity, across the image of a non-patterned area of a substrate.

FIG. 2 is a schematic illustration of an image 200, produced by vicinal illumination of a translucent substrate. Image 200 comprises rows, $R_1$ through $R_m$, and columns, $C_1$ through $C_n$, of pixel elements, represented by $P_{n,m}$. In this example, illumination is from the left side of the image 200. An inhomogeneity 202 appears in columns C4 through C6 of the image 200. The graph 204 illustrates one way in which the illumination intensity 206 can vary across a vicinally illuminated image, as the distance from the illumination source increases. The variation can be represented as a Gaussian as shown, or alternatively could be represented by other exponential, linear or non-linear functions. The result of the non-uniform illumination is that the image 200 can comprise multiple portions including; a portion where the pixels are saturated by the illumination (e.g. pixel columns C1 through C3), a portion where pixels receive too little illumination (e.g. pixel columns C5 through Cn), and an intervening portion where the illumination intensity is optimal for inspection (e.g. pixel column C4). As defined herein, an image portion having optimal illumination is defined as that portion of an image having an illumination intensity that is within the range of resolution of a device generating the images (e.g. within a reference range of illumination intensity). Image portions having optimal illumination are neither saturated (i.e. overexposed) or lacking in contrast (i.e. underexposed).

Each pixel $P_{n,m}$ in the image 200 comprises a gray scale level indicative of the illumination intensity received by the pixel. An imaging device having 12-bit gray scale resolution can divide the range of its sensitivity to illumination, into 4096 gray scale levels (i.e. $2^{12}$) where level 0 corresponds to the dark end of the range and level 4096 corresponds to the brightest end of the range. The portion of the image 200 having optimal illumination (e.g. column C4) for inspection will consist of a slice of the image 200, wherein the pixel elements comprise gray scale levels within the range of gray scale resolution of the imaging device (e.g. not saturated and not dark). The relative configuration of the imaging device, the illumination source, and the substrate can be chosen so that the portion of an image having optimal illumination will correspond to an unchanging subset of pixel elements (i.e. pixel column C4) within the imaging device.

In the example illustrated in FIG. 2, the portion of the image comprising column C4 is extracted from the image, for subsequent processing. While an extracted image portion can comprise one or more columns (or rows) of pixel elements, the following discussion will present an embodiment where the extracted image portion comprises a single column of pixel elements. The subset of pixels within the imaging device corresponding to the portion of the image 200 having optimal illumination can be selected manually by an operator viewing a display, or can be determined automatically by applying statistical methods to the illumination intensity of the pixel elements comprising the image. In the manual approach, an operator observing an image, by means of a display incorporated into the processor, can select the location within the image by identifying the column(s) of pixels that exhibit optimal contrast, for example pixel column C4. In an automated approach, the image is analyzed by a processor (item 120 in FIG. 1) wherein statistics are applied to the gray scale levels of the pixel elements. In an automated approach, an image of the substrate is analyzed by the processor. The average gray scale level is computed for each column of pixel elements. The pixel column having an average gray scale level (i.e. illumination intensity) that falls within a reference range can be selected as the column having optimal illumination. The reference range can be set to a value that approximates the center of the gray scale resolution range for the device generating the images. For example, given an imaging device capable of resolving 4096 gray scale levels, the reference level can be set to a value on the order of the midpoint of the devices resolution range, i.e. level 2048. In other approaches, the skew and kurtosis of the distribution of gray scale levels within an image portion, can be computed by the processor. Skew and kurtosis can be used to augment the selection process, for example, by identifying pixel columns having a more nearly uniform distribution of gray scale levels.

Figure 3:
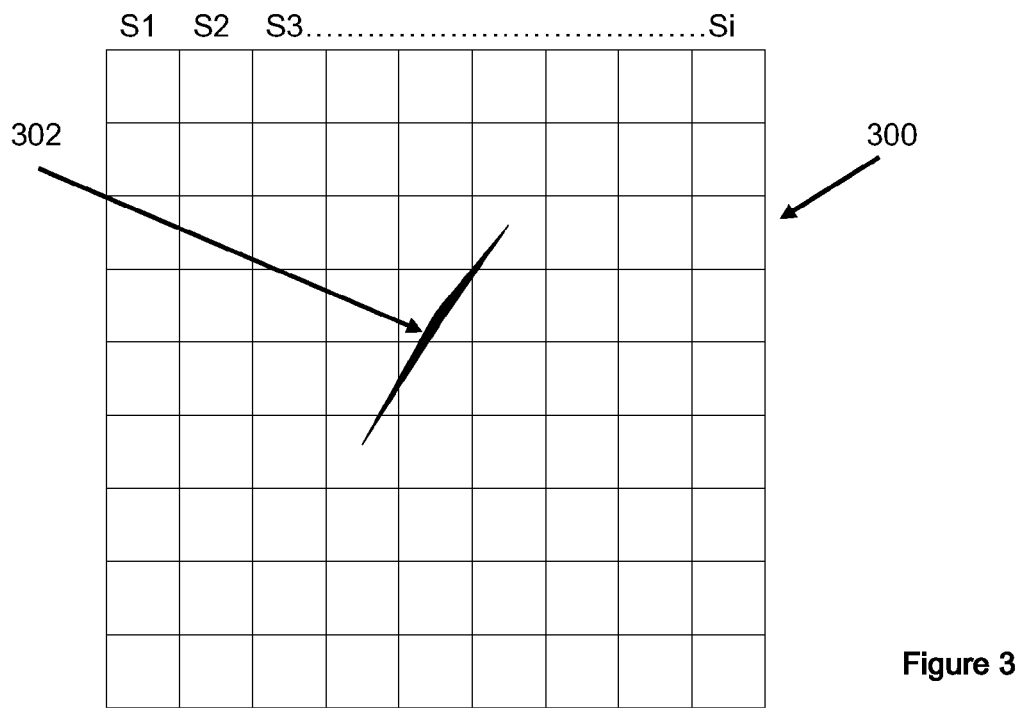
FIG. 3 is a schematic illustration of a composite image.

FIG. 3 is a schematic illustration of a composite image 300, comprising a reconstruction of image portions (i.e. slices, $S_1$ through $S_i$) extracted from a plurality of generated images. The inhomogeneity 302 is observable over a greater length of the inhomogeneity in the composite image 300, as compared to the raw image (200 in FIG. 2). Composite image 300 can include aligned extracted image portions, or in other embodiments, can include aligned portions of the extracted image portions.

Figure 4:
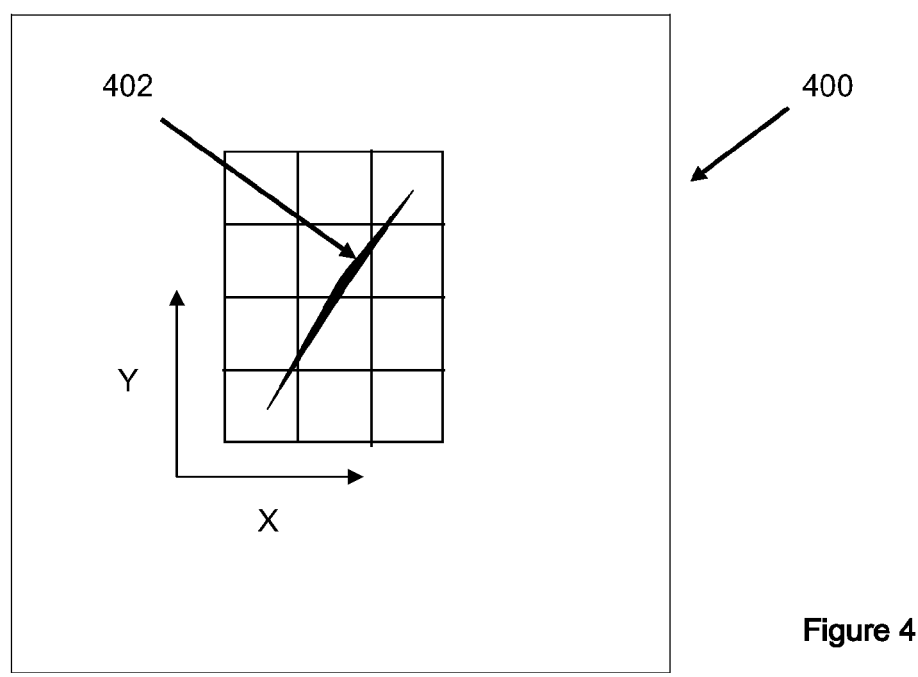
FIG. 4 is a schematic illustration of a composite image processed by enhancement and object detection algorithms.

FIG. 4 is a schematic illustration of a composite image 400 that has been processed with image enhancement and object detection algorithms. An image enhancement algorithm can be applied to the composite image to enhance the contrast of the edges of any inhomogeneities (i.e. features such as cracks, chips, voids etc.) that may be present in the composite image. An object detection algorithm can be applied to an enhanced composite image to determine if features are present in the composite image, and characterize the extents of any features that are present. The object detection algorithm can be used to return the number of pixels in the "x" and "y" directions occupied by the inhomogeneity 402. In this example, the inhomogeneity 402 extends three pixels in the x direction and four pixels in the y direction. The extents of the inhomogeneity in normal dimensional units can be obtained by applying a scaling factor, characteristic of the imaging device and the processor, to the unit pixel dimensions.

Figure 5:
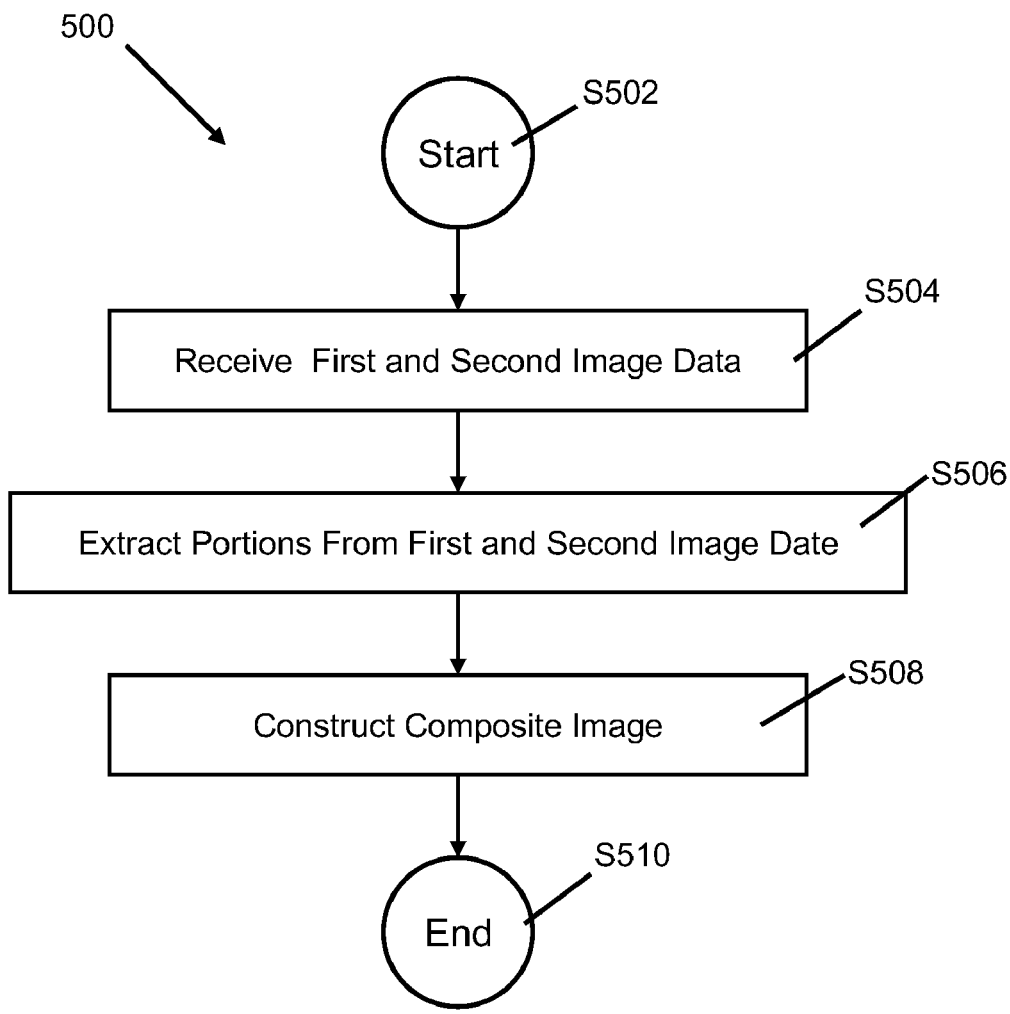
FIG. 5 is a flow-chart schematic illustrating one embodiment of a method according to the present invention.

FIG. 5 is a schematic flow-chart of an embodiment 500 of a method for inspecting substrates according to the invention. The process starts at step S502. At step S504, first and second image data sets including, respectively, first and second vicinally illuminated images of non-patterned areas of the substrate are received. There being a relative displacement between the substrate and the device generating the images, between generation of the first and second data sets. At step S506, first and second portions are extracted, respectively, from the first and second image data sets. The extracted portions can have an illumination intensity within a reference range. At step S508 the extracted image portions are aligned to construct a composite image of a non-patterned area of the substrate. Alternatively at step S508, the composite image can be constructed of aligned portions of the extracted image portions. The process ends at step S510.

Figure 6:
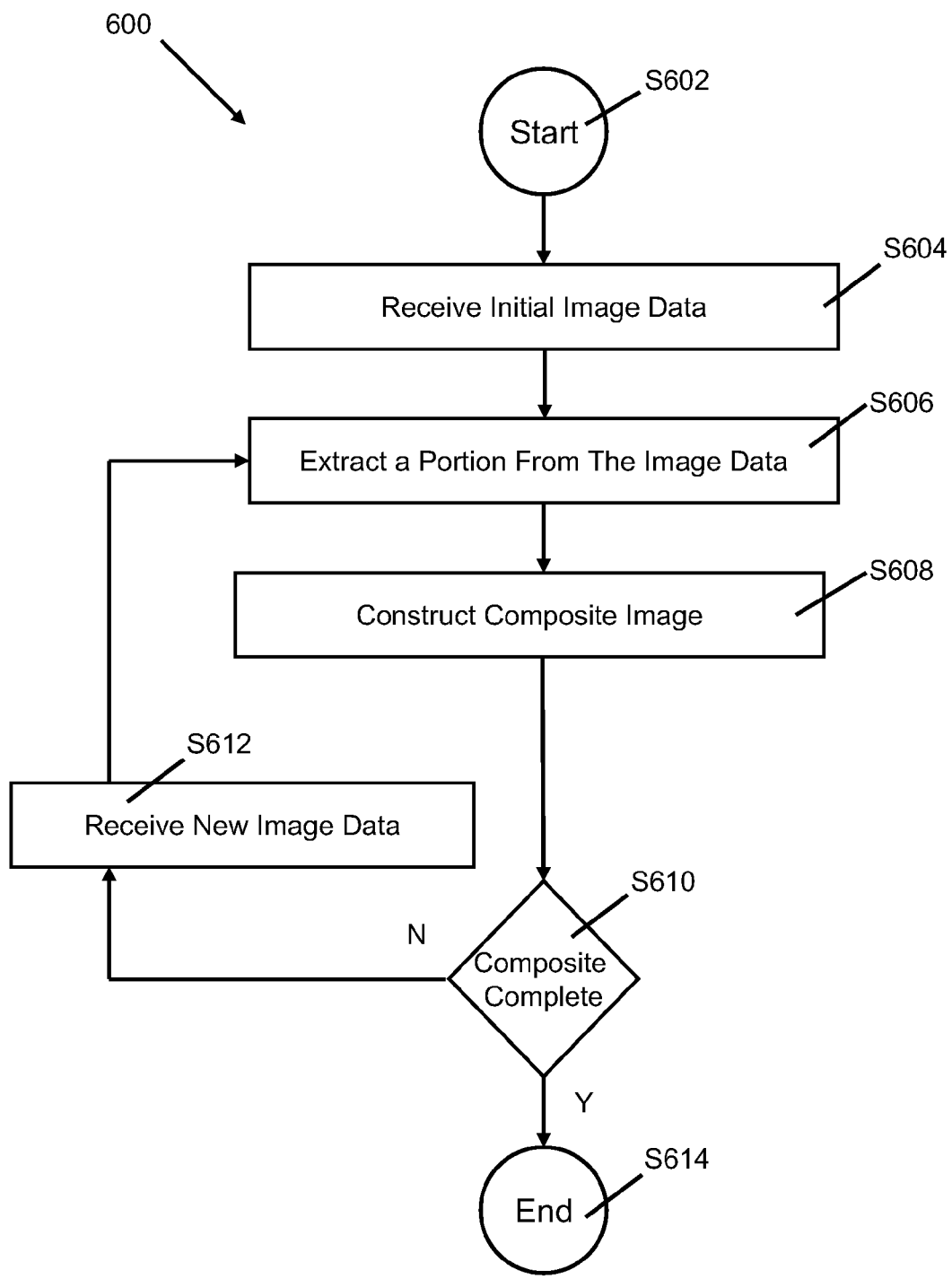
FIG. 6 is a flow-chart schematic illustrating another embodiment of a method according to the present invention.

FIG. 6 is a schematic flow-chart of another embodiment 600 of a method for inspecting substrates according to the invention. The process starts at step S602. At step S604 data comprising an initial vicinally illuminated image of a non-patterned area of the substrate is received. A portion (e.g. slice) is extracted from the initial received image data in step S606. A composite image is constructed at step S608, wherein the extracted image portion is aligned and added to the composite image. If at step S610 the composite image is completed (i.e. the area of interest of the substrate has been imaged) the process terminates at S614. If the composite image is not completed, a new set of image data is received at S612. The new set of image data of a non-patterned area on the substrate having been generated following a relative displacement between the substrate and the device generating the images. A new portion is extracted from the new image data set in step S606, and the newly extracted image portion is aligned and added to the composite image at step S608. Steps S610, S612, S606 and S608 are repeated until the composite image of a non-patterned area is completed, as determined at step S610, whereupon the process ends at step S614.

Figure 7:
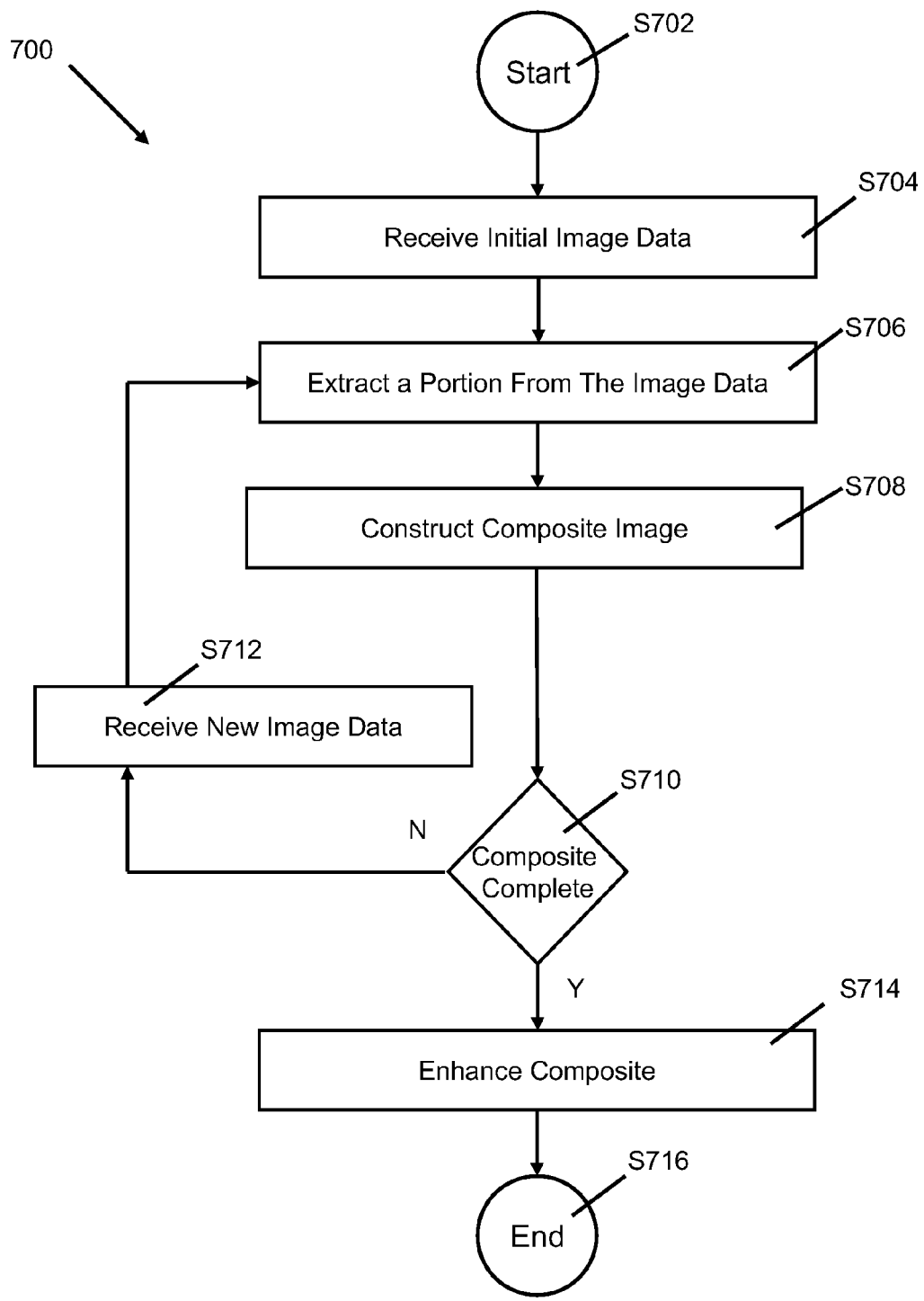
FIG. 7 is a flow-chart schematic illustrating another embodiment of a method according to the present invention.

FIG. 7 is a schematic flow-chart of another embodiment 700 of a method for inspecting non-patterned areas of substrates according to the invention. The process starts at step S702. At step S704 data comprising an initial vicinally illuminated image of a non-patterned area of the substrate is received. A portion is extracted from the initial received image data in step S706. A composite image is constructed at step S708, wherein the extracted image portion is aligned and added to the composite image. If at step S710 the composite image is completed (i.e. an area of interest of the sample has been imaged) the process proceeds to step S714. If the composite image is not completed at step S710, a new set of image data is received at S712. The new image data set having been generated following a relative displacement between the substrate and the device generating the images. A new portion is extracted from the new image data set in step S706, and the newly extracted image portion is aligned and added to the composite image at step S708. Steps S710, S712, S706 and S708 are repeated until the composite image is completed, as determined at step S710, whereupon the process proceeds to step S714. At step S714 an enhancement algorithm is applied to the composite image. The enhancement algorithm enhances the contrast of the edges of any inhomogeneities that may be present in the composite image of a non-patterned area of the substrate. The process then ends at step S716.

Figure 8:
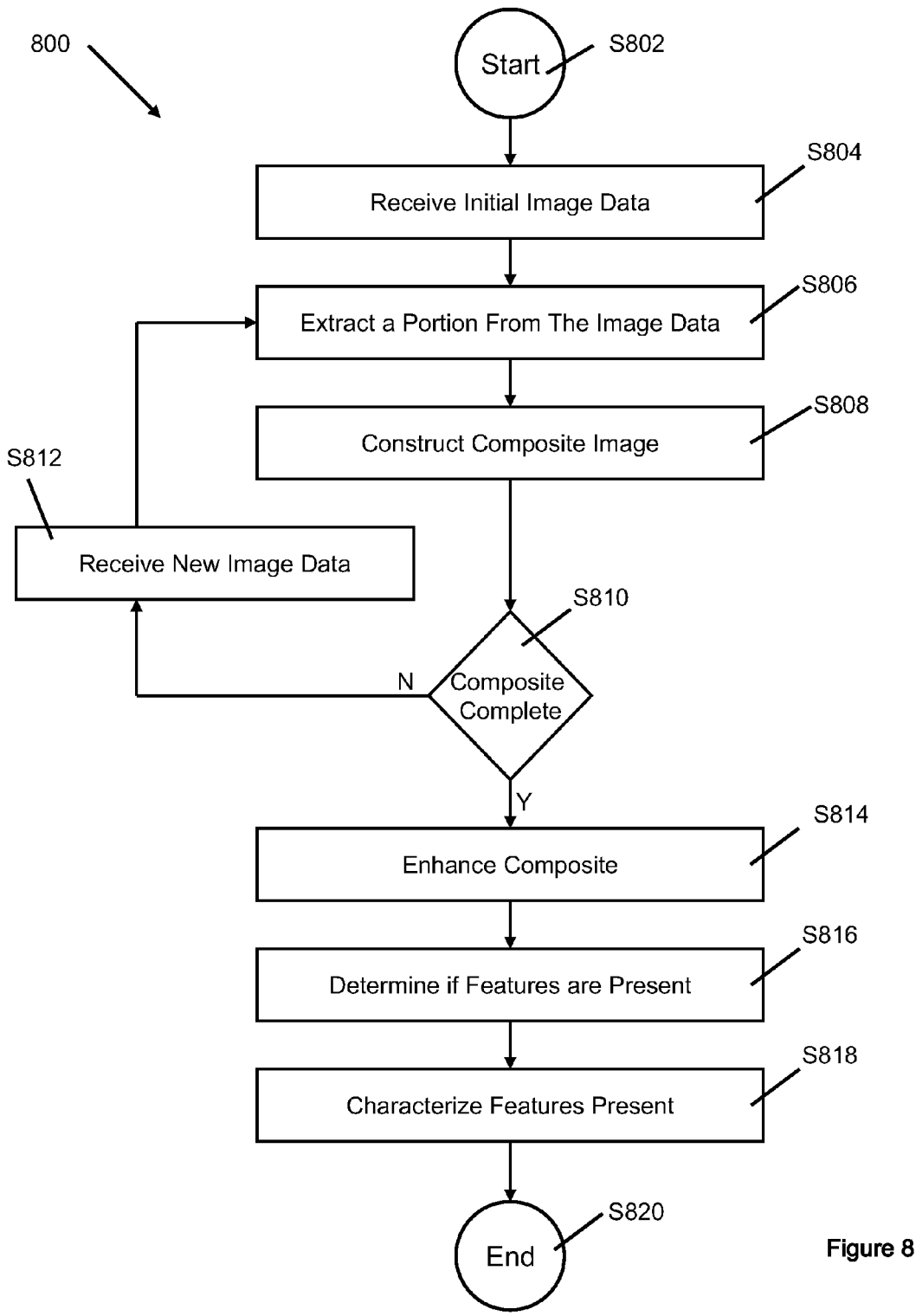
FIG. 8 is a flow-chart schematic illustrating another embodiment of a method according to the present invention.

FIG. 8 is a schematic flow-chart of another embodiment 800 of a method for inspecting substrates according to the invention. The process starts at step S802. At step S804 data comprising an initial vicinally illuminated image of a non-patterned ara of the substrate is received. A portion is extracted from the initial received image data in step S806. A composite image of a non-patterned area is constructed at step S808, wherein the extracted image portion is aligned and added to the composite image. If at step S810 the composite image is completed (i.e. an area of interest of the sample has been imaged) the process proceeds to step S814. If the composite image is not completed at step S810, a new set of image data is received at S812. The new image data set having been generated following a relative displacement between the substrate and the device generating the images. A new portion is extracted from the new image data set in step S806, and the newly extracted image portion is aligned and added to the composite image at step S808. Steps S810, S812, S806 and S808 are repeated until the composite image of the non-patterned area of interest is completed, as determined at step S810, whereupon the process proceeds to step S814. At step S814 an enhancement algorithm is applied to the composite image. The enhancement algorithm enhances the contrast of the edges of any inhomogeneities that may be present in the composite image. At step S816, an object detection algorithm is applied to the enhanced composite image. The object detection algorithm can determine if features (e.g. cracks, chips, voids, etc.) are present within the enhanced composite image of the non-patterned area. At step S818, if features are present within the enhanced composite image, an object detection algorithm can return the extents of the features. Steps S816 and S818 are illustrated as two independent steps for clarity, but can alternatively be combined into one process step (i.e. one application of an object detection algorithm). The process then ends at step S820. It should also be noted that in alternative embodiments, the object detection algorithm illustrated by steps S816 and S818, can be applied directly to a composite image at step S808 or S810.

Figure 9:
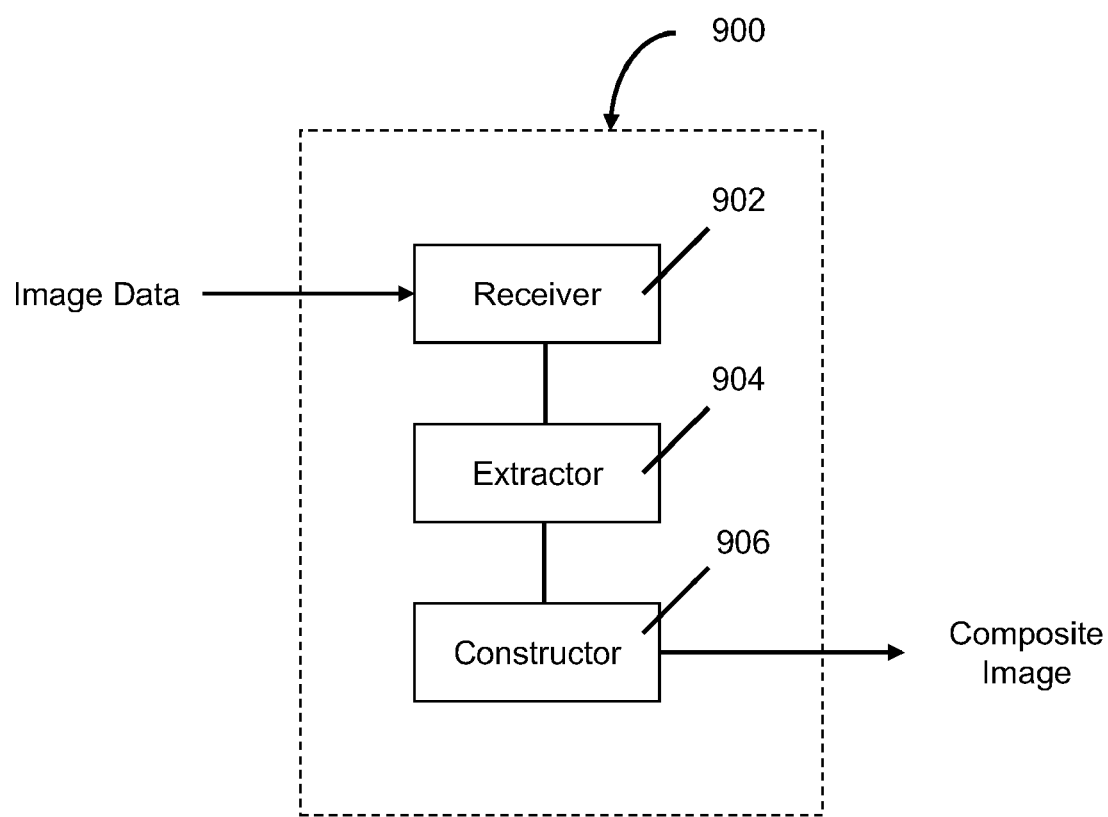
FIG. 9 is a schematic illustration of an embodiment of an apparatus according to the present invention.

FIG. 9 is a schematic illustration of an embodiment of a device 900 for inspecting substrates. Device 900 comprises a receiver 902 operatively configured to receive image data, the image data including an image of a non-patterned area of the substrate. The received image data may comprise data directly input from a digital imaging device (e.g. item 110 in FIG. 1) or alternatively, the received image data may comprise data obtained from the conversion of photographic images (e.g. hardcopy images) into a data format, such as by a scanner, the data thus generated being received by the receiver 902. The receiver 902 is operatively connected to an extractor 904. The extractor 904 is operatively configured to extract a portion from the image data received by the receiver 902. The portion of an image extracted by the extractor 904 can comprise that portion of the received image data having an illumination intensity within a reference range. The extractor 904 is operatively connected to a constructor 906. The constructor 906 is operatively configured to align and assemble the image portions extracted by the extractor 904, into a composite image of a non-patterned area of interest on the substrate. In an alternative embodiment, the constructor 906 can be operatively configured to align and assemble portions of the extracted image portions into a composite image.

Figure 10:
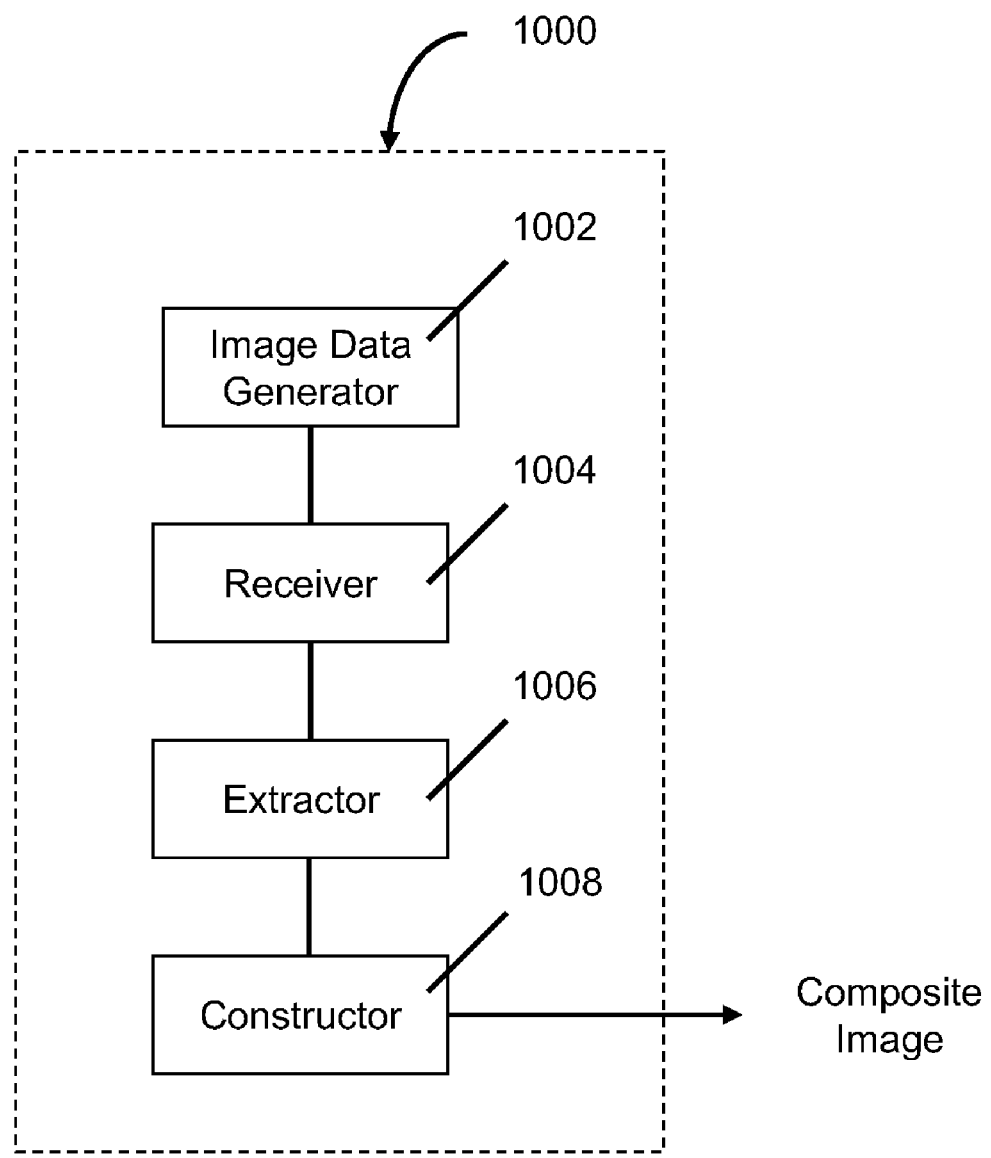
FIG. 10 is a schematic illustration of another embodiment of an apparatus according to the present invention.

FIG. 10 is a schematic illustration of another embodiment of a device 1000 for inspecting substrates. Device 1000 can comprise an image data generator 1002, operatively configured to generate image data including images of non-patterned areas of the surface of the substrate. The image data generator 1002 can include an imaging device such as a camera, a digital camera, a digital line camera, or a scanner for converting hard copy images (e.g. photographs) into a data format. The image data generator 1002 is operatively connected to a receiver 1004. The receiver 1004 is operatively configured to receive image data from the image data generator 1002. The receiver 1004 is operatively connected to an extractor 1006. The extractor 1006 is operatively configured to extract a portion from the image data received by the receiver 1004. The portion of an image extracted by the extractor 1006 can comprise that portion of the received image data having an illumination intensity within a reference range. The extractor 1006 is operatively connected to a constructor 1008. The constructor 1008 is operatively configured to align and assemble the image portions extracted by the extractor 1006, into a composite image of a non-patterned area of the substrate. In an alternative embodiment, the constructor 1008 can be operatively configured to align and assemble portions of the extracted image portions into a composite image.

Figure 11:
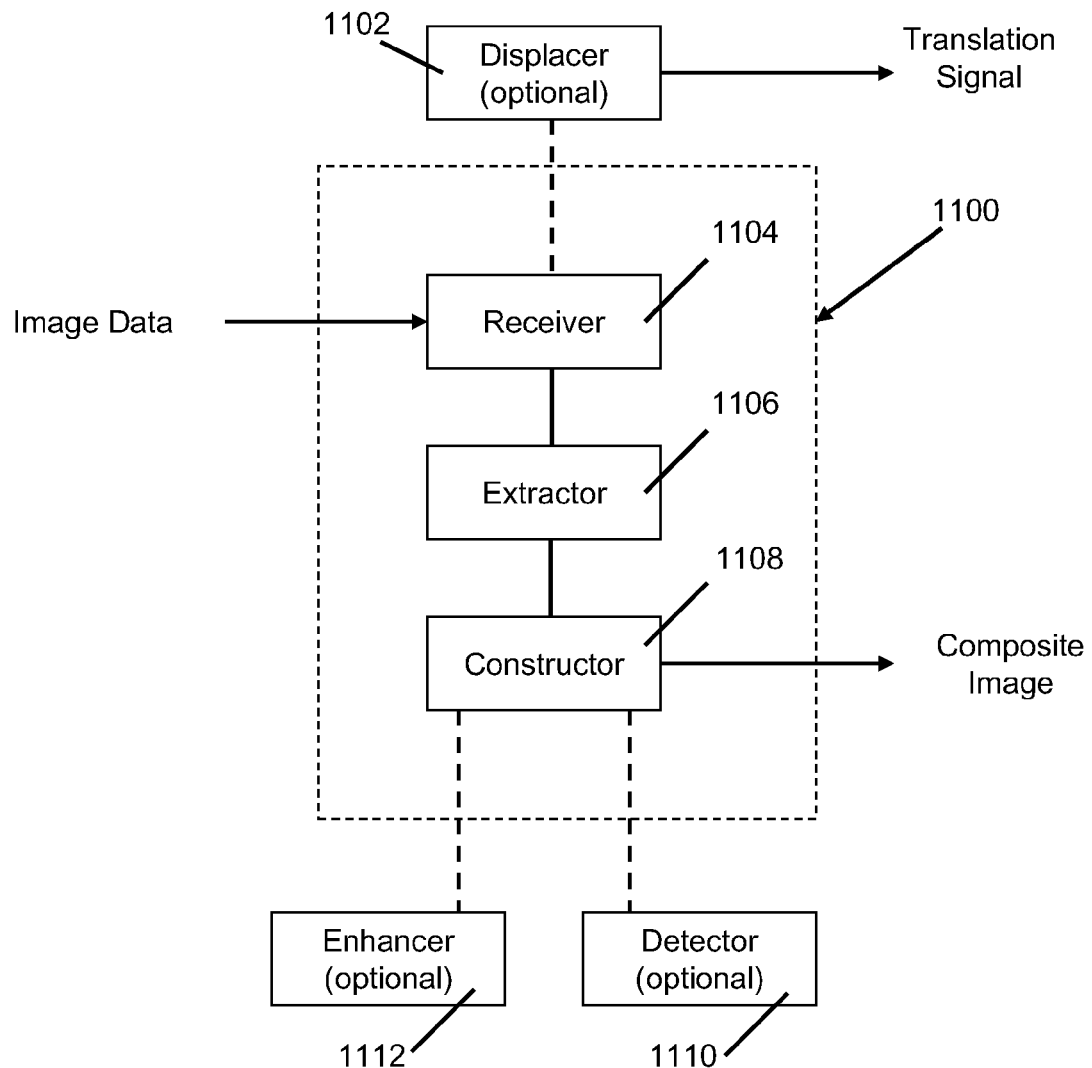
FIG. 11 is a schematic illustration of another embodiment of an apparatus according to the present invention.

FIG. 11 is a schematic illustration of another embodiment of a device 1100 for inspecting substrates. Device 1100 can comprise a receiver 1104 operatively configured to receive image data of non-patterned areas of a translucent material. The received image data may comprise data directly input from a digital imaging device (e.g. item 110 in FIG. 1) or alternatively, the received image data may comprise data obtained by converting photographic images into a data format, such as by a scanner. The receiver 1104 is operatively connected to an extractor 1106. The extractor 1106 is operatively configured to extract a portion from the image data received by the receiver 1104. The portion of an image extracted by the extractor 1106 can comprise that portion of the received image data having an illumination intensity within a reference range. The extractor 1106 is operatively connected to a constructor 1108. The constructor 1108 is operatively configured to align and assemble the image portions extracted by the extractor 1106, into a composite image of an non-patterned area of a translucent material. In an alternative embodiment, the constructor 1108 can be operatively configured to align and assemble portions of the extracted image portions into a composite image. An optional displacer 1102 is operatively configured to control the relative displacement between the substrate and a device generating the images, and is operatively connected to the receiver 1104. The displacer can generate a signal controlling the translation of a stage supporting the substrate, or alternatively the signal can be used to control the translation of the device generating the images. An optional enhancer 1112 is operatively configured to enhance images and is operatively connected to the constructor. An optional detector 1110 is operatively configured to detect features that may be present in the images, and is operatively connected to the constructor 1108.

As illustrated in FIG. 11, embodiments of inspection device 1100 can include a receiver 1104, an extractor 1106 and a constructor 1108, in combination with the optional components, a displacer 1102, an enhancer 1112 and a detector 1110, the optional components included either singly, in pairs or as a group. For example embodiments of the device 1100 can comprise:

a receiver, an extractor, a constructor, and a displacer, or, a receiver, an extractor, a constructor, and an enhancer, or, a receiver, an extractor, a constructor, and a detector, or, a receiver, an extractor, a constructor, a displacer, and an enhancer, or a receiver, an extractor, a constructor, a displacer, and a detector, or a receiver, an extractor, a constructor, an enhancer and a detector, or a receiver, an extractor, a constructor, a displacer, an enhancer and a detector.

The optional components including the displacer 1102, the enhancer 1112 and the detector 1110 can in some embodiments be incorporated directly into the structure of device 1100 or may alternatively exist outside of the structure of device 1100, and be operatively connected to the structure of device 1100.

EXAMPLE

In an exemplary application, the homogenous surface (i.e. an unpatterned area) of a piezoelectric (PZT) ceramic substrate approximately 6 mm square and 3 mm thick was inspected according to the present invention. A halogen illumination source with a fiber optic cable was used to illuminate an area on the surface of the substrate. The output head of the fiber optic cable was supported approximately 2.5 mm above the surface of the substrate, and focused the illumination into a narrow strip, approximately 3 mm wide and 4 cm long. A non-patterned area on the surface of the sample, approximately 0.25 mm away from the illuminated area, was observed by a digital camera having 7.4 μm pixel elements, and 12 bit gray scale resolution. It was found that a camera capable of resolving 12 bits, or 4096 levels of gray scale, was preferable to a camera capable of resolving 8 bits, or 256 levels of gray scale. A camera capable of distinguishing a greater number of gray scale levels (i.e. a higher bit number) improves the sensitivity of the method to detecting inhomogeneities.

By calibration it was determined that the 7.4 μm pixel width corresponded to an observable distance (per pixel width) of 12.2 μm on the surface of the substrate, equating to a system magnification factor of approximately 1.65×. The incremental distance by which the substrate was translated relative to the illumination source and imaging device, between generating images of the non-patterned area of the substrate was set to substantially equal the 12.2 μm imaging width of the pixel elements in the camera. Setting the incremental distance the substrate is translated, to equal the imaging width of the pixel elements in the camera is not critical to practicing the method. As described below for this example, each portion extracted from the images consisted of a column of pixels, one pixel wide. Multiple columns can be extracted as well, for which case the incremental distance the substrate is translated between sequential images, would be set to substantially equal the summed imaging width of the multiple of columns.

The inspection device used in this example comprised a personal computer (PC) with an image acquisition card for receiving images from the digital camera, and a displacer (i.e. a motion control card) for controlling the translation of a stage supporting the substrate. Commercially available software (LabVIEW™) was used to perform the image processing algorithms. It should be noted that other software products can be configured, to practice the method, including for example, Softwire™ and Matlab™.

Figure 12:
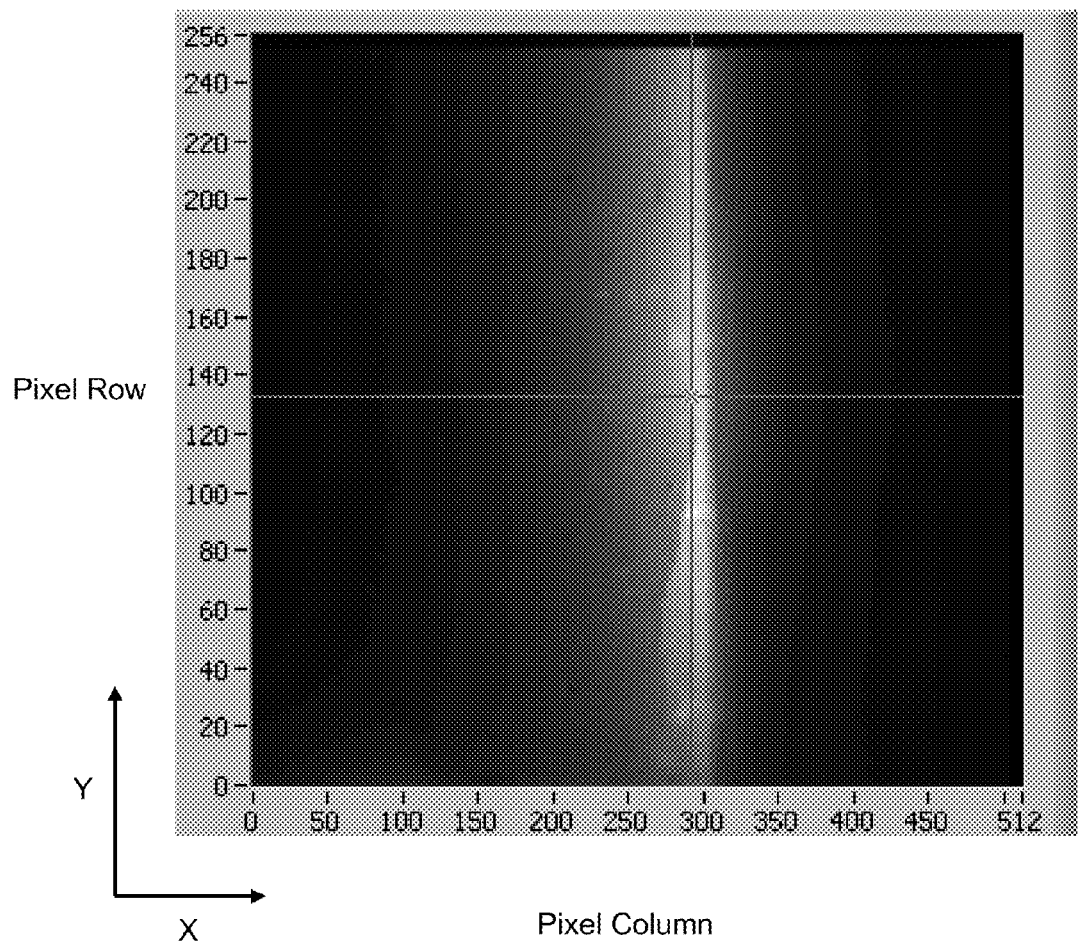
FIG. 12 is an example of an image of a substrate formed by vicinal illumination.

LabVIEW™ is a registered trademark of National Instruments Corporation, Austin, Tex., USA Softwire™ is a registered trademark of Softwire Technology, Middleboro, Mass., USA Matlab™ is a registered trademark of The MathWorks INC, Natick, Mass., USA FIG. 12 is an example of an image formed by vicinal illumination of a non-patterned area of a substrate. Illumination is from the right side in this image, with the edge of the fiber optic cable head positioned approximately adjacent to the pixel column at location 310 (on the horizontal scale). The cross hairs in FIG. 12 indicate the pixel column at location 292 (approximately 0.25 mm from the edge of the fiber optic cable head) as comprises the portion of the image having optimal contrast for observing inhomogeneities. Pixel columns to the right of column 292 (nearer the light source) are saturated, i.e. too bright for observation, and the illumination intensity can be seen to drop off rapidly in the columns to the left of column 292.

FIG. 12 illustrates that an inspector observing an unprocessed image of a vicinally illuminated substrate, can effectively observe only a very narrow slice of the area to be inspected on the substrate. This problem is one addressed by the methods and apparatus presented herein. The slice of the image comprising pixel column 292 is extracted from the image and stored in a composite array. The substrate is translated by the equivalent of one pixel imaging width (to the right, 12.2 µm in this example) and a subsequent image of the substrate was generated and received by the processor. The slice of the subsequent image, again comprising the information in pixel column 292 was extracted and stored in the composite array, adjacent and aligned to the previously extracted image portion. The process of translating the substrate, receiving an image of the non-patterned area, extracting an image portion, and storing the portion in a composite image array was repeated, until a composite image, comprising the non-patterned area of the substrate to be inspected was completed.

Figure 13:
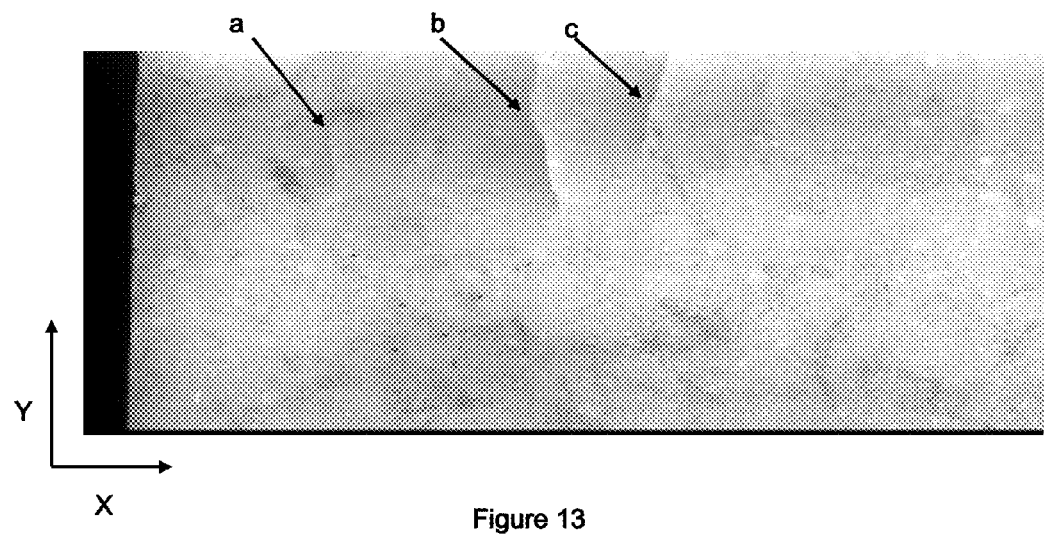
FIG. 13 is an example of a composite image, constructed of aligned portions of extracted image portions.

FIG. 13 is an example of a composite image of a non-patterned area of the substrate. By comparing FIG. 13 to FIG. 12, it can be seen that an inspector observing the composite image in FIG. 13, has a greater field of view of the substrate, having optimal contrast over the area of the substrate to be inspected. Cracks within the substrate are readily observable in the composite image (FIG. 13) at the locations marked "a", "b" and "c". An edge detection algorithm can now be applied to the composite image, to enhance the edges of the cracks for further analysis.

Figure 14:
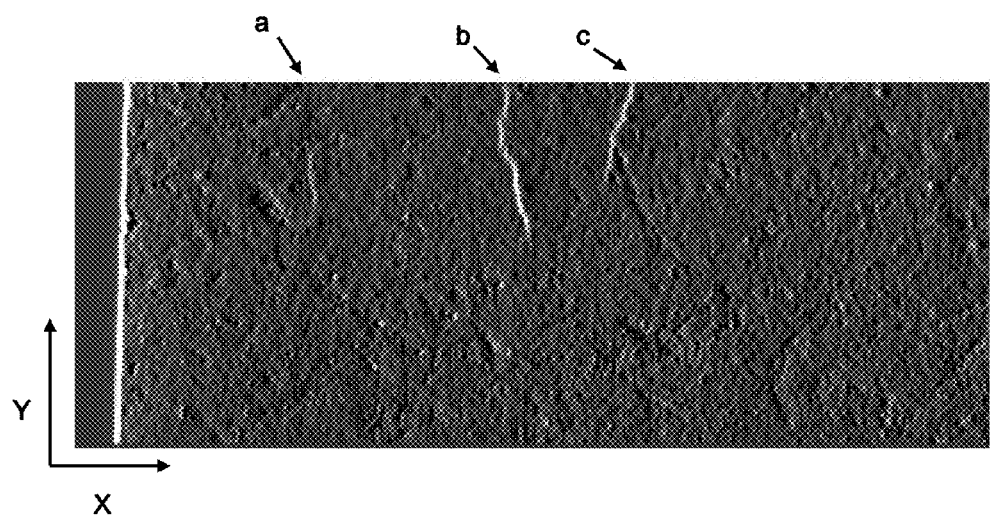
FIG. 14 is an example of a composite image, processed by an enhancement algorithm.

FIG. 14 is an example composite image of the non-patterned area of the substrate, processed by an edge enhancement filter. In this example, a 5×5 East-West gradient filter kernel was applied, following the convention that east is to the right of the image and west is to the left of the image. In vicinal illumination, the side of the crack facing the light source is brighter due to reflections from the crack interface, and the filter direction is chosen to match the illumination direction. In this example, the filter examined an area comprising a 5×5 pixel array and enhanced light to dark shifts in which the illumination source faces west. As can be seen in FIG. 14, the cracks stand out as bright objects against a dark background.

Figure 15:
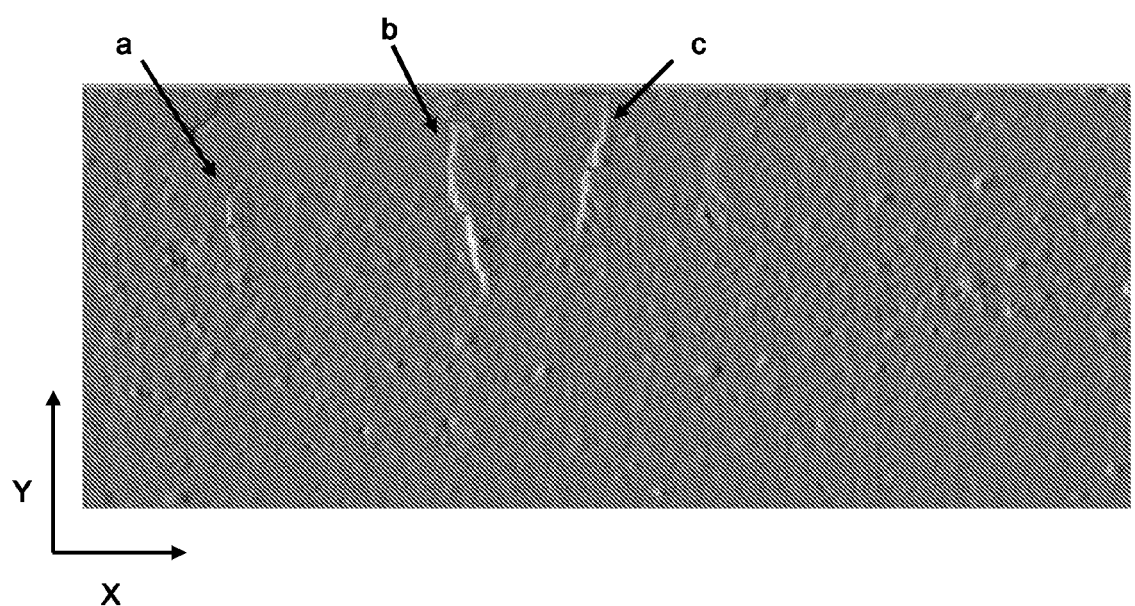
FIG. 15 is an example of a composite image, processed by enhancement and object detection algorithms.

FIG. 15 is an example of an enhanced composite image of the non-patterned processed by an object detection filter. After processing a composite image with an enhancement algorithm, cracks and other inhomogeneities, can be determined to be present, and the extents of the inhomogeneities measured, using an object detection algorithm that looks for objects (e.g. features such as cracks, chips, voids, etc.) having an intensity value above an arbitrary level. The extents of the crack can then be measured in pixels, i.e. how much the crack extends in the x and y-directions. With the knowledge that 1 pixel width equates to 12.2 µm, crack lengths in standard dimensional units can be computed from the extents as measured in pixels. As illustrated in FIG. 15, the object detection algorithm can overlay a "box" on each of the objects at "a", "b" and "c", and return the dimensions of the sides of the box.

Comparison of Measurements Obtained by Manual Inspection and Automated Inspection Methods Table 1 lists data obtained from a comparison of crack length measurements obtained by the automated method with those obtained manually by three independent inspectors. For the manual measurements, inspectors using a vicinally illuminated inspection station comprising a low power microscope with a calibrated graticule, measured the extent of the cracks corresponding to those labeled "b" and "c" in FIG. 11, along the "y"-direction.

TABLE 1

Comparison of Manual Inspection and Automated Inspection

| | Crack "b" (mm) | Crack "c" (mm) |
|---|---|---|
| Inspector #1 (manual) | 1.65 | 1.09 |
| Inspector #2 (manual) | 1.52 | 1.02 |
| Inspector #3 (manual) | 1.45 | 1.17 |
| Average of the Three Manual Inspections | 1.54 | 1.09 |
| Standard Deviation of the Three Manual Inspections | 0.10 | 0.08 |
| Automated Measurements According to The Method | 1.59 | 1.18 |

The average and standard deviation of the three manual measurements obtained by the inspectors for cracks "b" and "c" are listed in Table 1. Measurements of the lengths of cracks "b" and "c" obtained by the present automated method, are also listed in the table. As can be seen by a comparison of the measurements, the results obtained by the automated method according to the present invention, are within the range expected from the manual inspections.

Having thus described exemplary embodiments of the present invention, those skilled in the art will appreciate that the present invention can be implemented in other ways. The actual scope of the invention is intended to be defined in the following claims.

What is claimed is:

1. A method for inspecting a non-patterned area of a surface of a translucent substrate comprising:
    using a processor to perform the following:
        illuminating the translucent substrate by a light source with vicinal illumination, said vicinal illumination comprising illuminating an illuminated area of the translucent substrate, the illuminated area of the translucent substrate displaced from an imaged area of the translucent substrate, the imaged area comprising a sub-area of the non-patterned area, the imaged area imaged by an image generating device thereby generating images of the surface of the translucent substrate comprised of diffused reflected light from the light source;

receiving first image data representative of a first imaged area within the non-patterned area of the translucent substrate;

receiving second image data representative of a second imaged area within the non-patterned area of the translucent substrate, the second imaged area selected from an area abutting the first imaged area and an area overlapping the first imaged area;

extracting a first data subset from the first image data, the first data subset representative of a first portion of the non-patterned area;

extracting a second data subset from the second image data, said second data subset representative of a second portion of the non-patterned area, said first and second data subsets each having an illumination intensity within a reference range, the first portion of the non-patterned area being adjacent to and aligned with the second portion of the non-patterned area; and, constructing a composite image from the extracted first and second data subsets, the composite image comprising the adjacent and aligned first and second portions of the non-patterned area.

2. The method of claim 1 wherein said receiving first image data and said receiving second image data, includes receiving data having a gray scale resolution of eight bits or greater.

3. The method of claim 1 wherein said extracting said first and second data subsets includes setting the reference range to a value substantially equal to one half of the gray scale resolution of the image generating device.

4. The method of claim 1 further comprising the step of enhancing said composite image.

5. The method of claim 4 further comprising the step of detecting an object within an enhanced composite image.

6. The method of claim 5 further comprising the step of measuring an extent of the object detected within said enhanced composite image.

7. The method of claim 1 further comprising the step of detecting an object within said composite image.

8. The method of claim 7 further comprising the step of measuring an extent of the object detected within said composite image.

9. The method of claim 1 wherein the steps of extracting said first and second data subsets includes extracting first and second pixel arrays, from said first image data and said second image data respectively.

10. The method of claim 1 further comprising the steps of:
configuring said first and second portions of the non-patterned area to each comprise a reference length along the surface of the translucent substrate; and,
displacing the translucent substrate relative to the image generating device by a distance substantially equal to the reference length after the step of receiving the first image data and prior to the step of receiving the second image data.

11. The method of claim 1 further comprising the step of: rotating the translucent substrate by an angle on the order of 90 degrees.

12. An apparatus for inspecting a non-patterned area of a surface of a translucent substrate comprising:
a light source operatively arranged to illuminate an illuminated area of the translucent substrate;
an image generating device operatively arranged to generate images of imaged areas of the translucent substrate and image data sets representative thereof, the imaged areas of the translucent substrate comprising sub-areas of the non-patterned area, the imaged areas of the translucent substrate displaced from the illuminated area of the translucent substrate, thereby generating images of the surface of the translucent substrate comprised of diffused reflected light from the light source, the image generating device operatively connected to the light source;
a receiver operatively arranged to receive first and second image data representative of first and second imaged areas respectively within the non-patterned area of the translucent substrate, the second imaged area selected from an area abutting the first imaged area and an area overlapping the first imaged area, the receiver operatively connected to the image generating device;
an extractor operatively arranged to extract first and second image data subsets from the first and second image data respectively, the first and second image data subsets representative of first and second portions of the non-patterned area respectively, the first portion of the non-patterned area being adjacent to and aligned with the second portion of the non-patterned area, the first and second image data subsets having an illumination intensity within a reference range, said extractor operatively connected to said receiver; and,
a constructor operatively arranged to construct a composite image, said composite image including aligned portions of said extracted first and second image data subsets, said constructor operatively connected to said extractor.

13. The apparatus of claim 12 further comprising an enhancer operatively arranged to enhance said composite image, said enhancer operatively connected to said constructor.

14. The apparatus of claim 12 further comprising a detector operatively arranged to detect objects within said composite image, said detector operatively connected to said constructor.

15. The apparatus of claim 12 further comprising a displacer operatively arranged to control a relative displacement between the translucent substrate and the image generating device, said displacer operatively connected to said image generating device.

* * * * *